United States Patent
Chen et al.

(10) Patent No.: US 10,042,252 B2
(45) Date of Patent: Aug. 7, 2018

(54) EXTREME ULTRAVIOLET PHOTORESIST AND METHOD

(71) Applicant: Taiwan Semiconductor Manufacturing Co., Ltd., Hsin-Chu (TW)

(72) Inventors: Yen-Hao Chen, New Taipei (TW); Wei-Han Lai, New Taipei (TW); Chien-Wei Wang, Hsinchu County (TW); Chin-Hsiang Lin, Hsin-chu (TW)

(73) Assignee: TAIWAN SEMICONDUCTOR MANUFACTURING CO., LTD., Hsin-Chu (TW)

(*) Notice: Subject to any disclaimer, the term of this patent is extended or adjusted under 35 U.S.C. 154(b) by 0 days.

(21) Appl. No.: 15/412,856

(22) Filed: Jan. 23, 2017

(65) Prior Publication Data

US 2018/0149971 A1  May 31, 2018

Related U.S. Application Data

(60) Provisional application No. 62/428,266, filed on Nov. 30, 2016.

(51) Int. Cl.
| | |
|---|---|
| *G03F 7/004* | (2006.01) |
| *G03F 7/039* | (2006.01) |
| *G03F 7/038* | (2006.01) |
| *G03F 7/20* | (2006.01) |
| *G03F 7/16* | (2006.01) |

(Continued)

(52) U.S. Cl.
CPC .......... *G03F 7/0045* (2013.01); *C07C 381/12* (2013.01); *G03F 7/0382* (2013.01); *G03F 7/0392* (2013.01); *G03F 7/16* (2013.01); *G03F 7/2002* (2013.01); *G03F 7/2004* (2013.01);

(Continued)

(58) Field of Classification Search
CPC .......... G03F 7/004; G03F 7/2002; G03F 7/32; G03F 7/38; G03F 7/40; H01L 21/0274; C07C 381/12
USPC .... 430/270.1, 322, 325, 329, 330, 331, 942, 430/913
See application file for complete search history.

(56) References Cited

U.S. PATENT DOCUMENTS

| | | |
|---|---|---|
| 8,216,767 B2 | 7/2012 | Wang et al. |
| 8,323,870 B2 | 12/2012 | Lee et al. |

(Continued)

OTHER PUBLICATIONS

K. Subramanya Mayya et al., "EUV Sensitive Photo-Acid Generator Sans Chromophore," Proc. SPIE Proceedings vol. 7520, Lithography Asia 2009, 75200R (Dec. 11, 2009); 6 pages.

(Continued)

*Primary Examiner* — Amanda C Walke
(74) *Attorney, Agent, or Firm* — Haynes and Boone, LLP

(57) ABSTRACT

The present disclosure provides a method for lithography patterning in accordance with some embodiments. The method includes forming a photoresist layer over a substrate, wherein the photoresist layer includes a polymer, a sensitizer, and a photo-acid generator (PAG), wherein the PAG includes a first phenyl ring and a second phenyl ring both chemically bonded to a sulfur, the first and second phenyl rings being further chemically bonded with enhanced sensitivity; performing an exposing process to the photoresist layer; and developing the photoresist layer, thereby forming a patterned photoresist layer.

20 Claims, 10 Drawing Sheets

(51) Int. Cl.
*G03F 7/26* (2006.01)
*G03F 7/40* (2006.01)
*H01L 21/027* (2006.01)
*G03F 7/38* (2006.01)
*C07C 381/12* (2006.01)

(52) U.S. Cl.
CPC .............. *G03F 7/26* (2013.01); *G03F 7/38* (2013.01); *G03F 7/40* (2013.01); *H01L 21/0274* (2013.01)

(56) References Cited

U.S. PATENT DOCUMENTS

| | | | |
|---|---|---|---|
| 8,580,117 | B2 | 11/2013 | Kao et al. |
| 8,658,344 | B2 | 2/2014 | Wang et al. |
| 8,715,919 | B2 | 5/2014 | Chang et al. |
| 8,741,551 | B2 | 6/2014 | Wu et al. |
| 9,477,149 | B2 * | 10/2016 | Namai ............... C07D 307/93 |
| 2011/0112306 | A1 * | 5/2011 | Nagamori ............. C07C 25/18 548/435 |
| 2013/0323641 | A1 | 12/2013 | Chang |
| 2014/0011133 | A1 | 1/2014 | Liu et al. |
| 2014/0017615 | A1 | 1/2014 | Chang |
| 2014/0017616 | A1 | 1/2014 | Chang |
| 2014/0065843 | A1 | 3/2014 | Chang et al. |
| 2014/0117563 | A1 | 5/2014 | Yu et al. |
| 2014/0120459 | A1 | 5/2014 | Liu et al. |
| 2014/0186773 | A1 | 7/2014 | Chang |
| 2014/0255850 | A1 | 9/2014 | Chang et al. |
| 2014/0272709 | A1 | 9/2014 | Liu et al. |
| 2014/0272726 | A1 | 9/2014 | Chang |
| 2014/0273521 | A1 | 9/2014 | Wu et al. |
| 2014/0377706 | A1 * | 12/2014 | Hatakeyama ............. G03F 7/32 430/296 |
| 2015/0086926 | A1 * | 3/2015 | Ohashi ................. C07C 381/12 430/285.1 |
| 2015/0241779 | A1 * | 8/2015 | Enomoto ................ G03F 7/203 430/270.1 |
| 2016/0004160 | A1 * | 1/2016 | Tagawa ..................... G03F 7/38 430/296 |
| 2016/0357103 | A1 * | 12/2016 | Nagahara ................ G03F 7/38 |
| 2017/0052448 | A1 * | 2/2017 | Nakagawa ........... G03F 7/0397 |
| 2017/0052449 | A1 * | 2/2017 | Nakagawa ........... C07D 317/72 |
| 2017/0075221 | A1 * | 3/2017 | Nakagawa ............. G03F 7/322 |
| 2017/0075224 | A1 * | 3/2017 | Nakagawa ............. G03F 7/203 |
| 2017/0131633 | A1 * | 5/2017 | Nakagawa ........... G03F 7/0046 |
| 2017/0131634 | A1 * | 5/2017 | Nakagawa ........... G03F 7/0046 |

OTHER PUBLICATIONS

James W Thackeray; "Materials Challenges for Sub-20-Nm Lithography," Published in: Journal of Micro/Nanolith MEMS MOEMS. vol. 10; Issue 3, (Aug. 18, 2011), 9 pages.

* cited by examiner

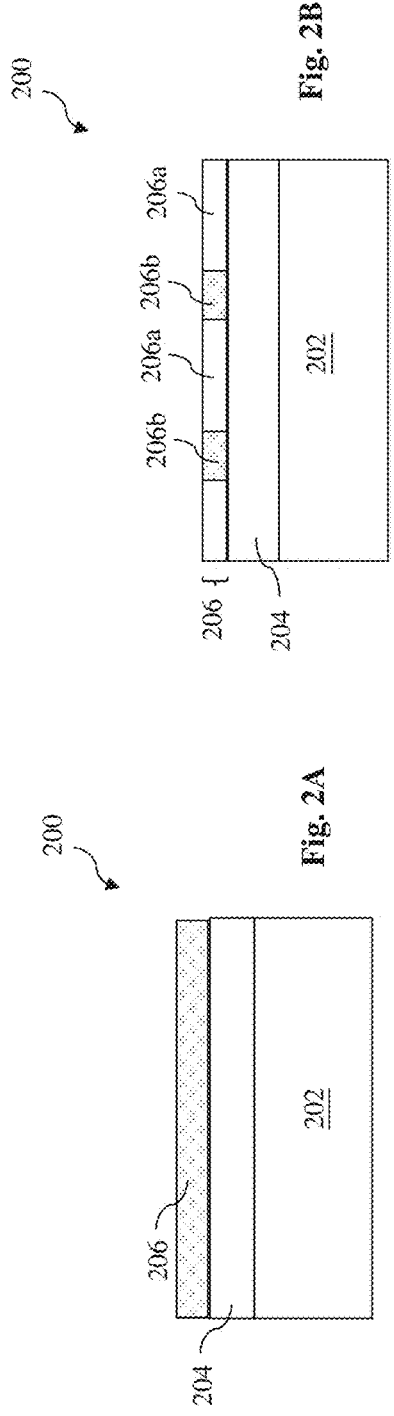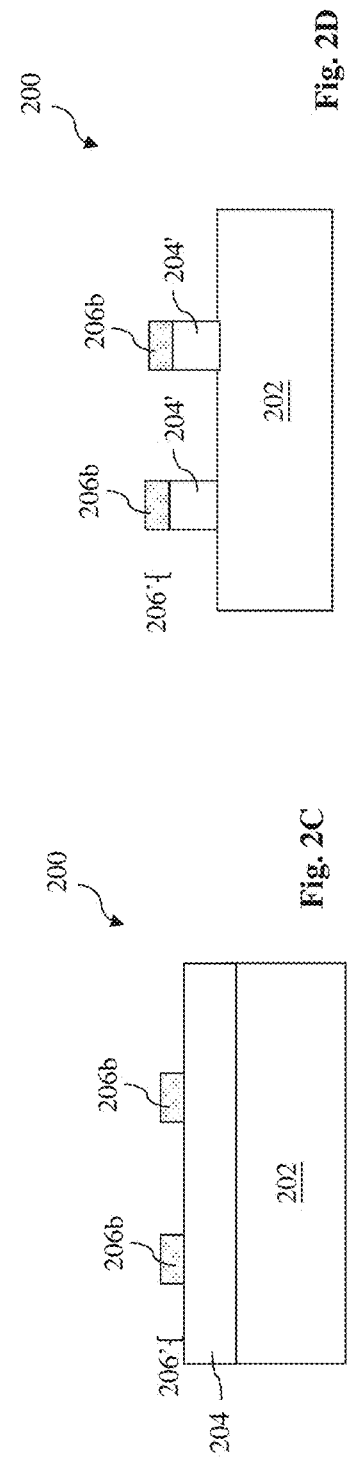

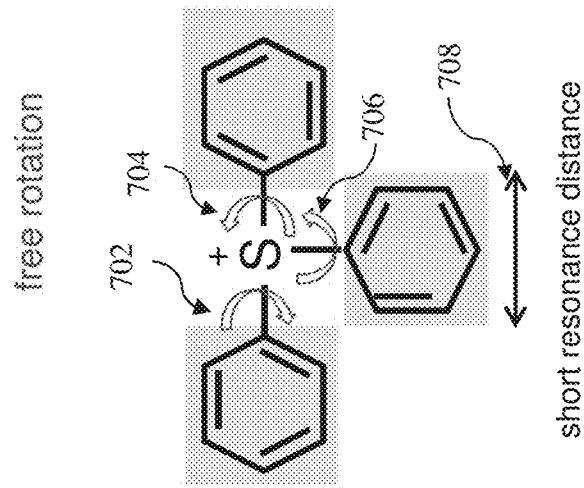

EXTREME ULTRAVIOLET PHOTORESIST AND METHOD

PRIORITY DATA

This application claims the benefit of U.S. Provisional Application 62/428,266 entitled "EXTREME ULTRAVIOLET PHOTORESIST AND METHOD," filed Nov. 30, 2016, herein incorporated by reference in its entirety.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs. For example, as the semiconductor fabrication continues to shrink pitches below 20 nm nodes, traditional i-ArF were confronted a huge challenge. The optical restriction leads to resolution and lithography performance that cannot meet targets. Extreme ultraviolet (EUV) lithography has been utilized to support critical dimension (CD) requirements of smaller devices. EUV lithography employs scanners using radiation in the EUV region, having a wavelength of about 1 nm to about 100 nm. Some EUV scanners provide 4× reduction projection printing onto a resist film coated on a substrate, similar to some optical scanners, except that the EUV scanners use reflective rather than refractive optics. EUV lithography has imposed a complex set of requirements upon the resist film.

The photo acid generator (PAG) in ArF resist absorbs 193 nm wave and generates photoacid, and the acid will proceed 1000 times chemical amplifier reaction (CAR) and deprotect acid labile group (ALG). Different with 193 nm ArF resist, EUV will let sensitizer generate secondary electron. The secondary electron's energy is similar with 193 nm energy and is absorbed by PAG, which further generates photoacid and proceeds to CAR reaction after absorbing secondary electron, like 193 nm ArF resist. However, due to low source power for EUV tool, photoresist is not efficient to generate enough acid for desired resolution. What are needed are a photoresist and a method using the photoresist to have improvements in this area.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 2A, 2B, 2C, 2D and 2E illustrate cross sectional views of a semiconductor structure at various fabrication stages, in accordance with some embodiments.

FIG. 7 illustrates a chemical structure of the cation in the PAG of FIG. 6 in accordance with an embodiment.

DETAILED DESCRIPTION

Figure 1:
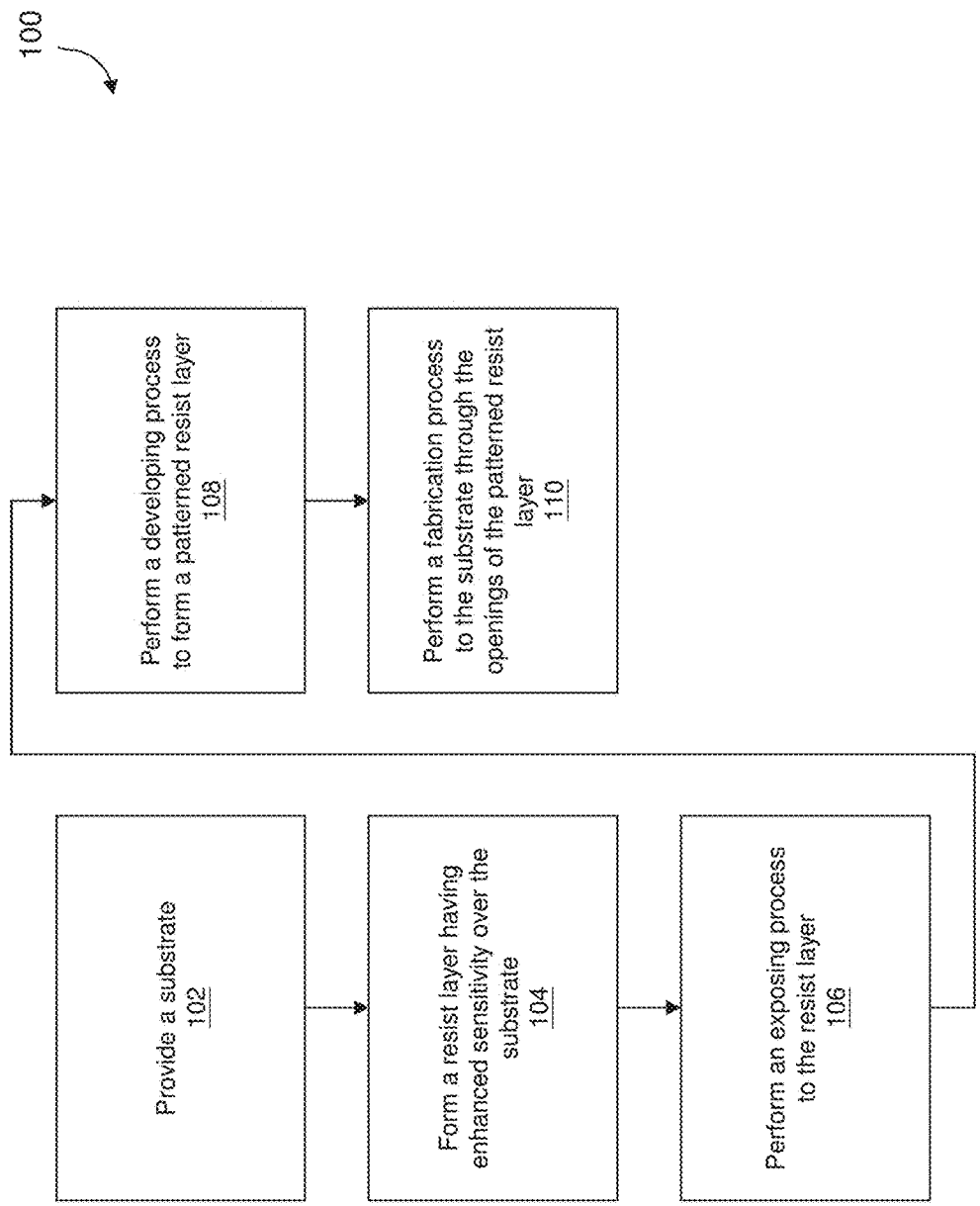
FIG. 1 illustrates a flow chart of a lithography patterning method in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure is generally related to methods for semiconductor device fabrication, and more particularly to compositions of photosensitive films in extreme ultraviolet (EUV) lithography and methods of using the same. In lithography patterning, after a resist film is exposed to a radiation, such as a EUV radiation (or alternatively other radiation, such as an electron beam), it is developed in a developer (a chemical solution). The developer removes portions (such as exposed portions as in a positive-tone photoresist or unexposed portions as in a negative-tone photoresist) of the resist film, thereby forming a resist pattern which may include line patterns and/or trench patterns. The resist pattern is then used as an etch mask in subsequent etching processes, transferring the pattern to an underlying material layer. Alternatively, the resist pattern is then used as an ion implantation mask in subsequent ion implantation processes applied to the underlying material layer, such as an epitaxial semiconductor layer.

Generally, to produce the smallest possible circuitry, most advanced lithography systems are designed to use light of very short wavelength such as for example, deep-ultraviolet light at a wavelength at or below 200 nm, or extreme ultraviolet (EUV) in the region of about 13.5 nm. Such light sources are relatively weak, so the photosensitive films (e.g., a photoresist) need to be designed to utilize this light as efficiently as possible. Essentially photoresists used today for microelectronic/nanoelectronic fabrication employ the concept of chemical amplification to enhance the efficiency of light utilization.

A photoresist that employs the chemical amplification is generally referred to as a "chemically amplified resist (CAR)". The photoresist includes a polymer that resists to etching or ion implantation during semiconductor fabrication; an acid generating compound (e.g., photo acid generator (PAG)); and a solvent. In some examples, the polymer also includes at least one acid labile group (ALG) that responds to acid. PAG absorbs radiation energy and generates acid. The polymer and the PAG are mixed in the solvent before the photoresist is applied to a workpiece, such as a semiconductor wafer, during a lithography process. The PAG is not sensitive to the EUV radiation. That is, advance to improve lithography efficiency (e.g., resolution/contrast, line-width-roughness, and sensitivity) encounters issues. Therefore, the photoresist further includes a sensitizer serving to increase the sensitivity of the photoresist. The sensitizer is sensitive to EUV radiation, absorbs EUV radiation and generates electron. Thus, the PAG absorbs electron and generates acid. However, due to limited source power of a EUV lithography system, an existing photoresist cannot provide imaging effect during a lithography exposure process with desired resolution and contrast. The disclosed photoresist includes a PAG with a certain chemical structure for increased sensitivity. The photoresist and the lithography method are further described below.

FIG. 1 is a flow chart of a method 100 of patterning a substrate (e.g., a semiconductor wafer) according to various aspects of the present disclosure in some embodiments. The method 100 may be implemented, in whole or in part, by a system employing advanced lithography processes such as deep ultraviolet (DUV) lithography, extreme ultraviolet (EUV) lithography, electron beam (e-beam) lithography, x-ray lithography, and/or other lithography processes to improve pattern dimension accuracy. In the present embodiment, EUV and/or e-beam lithography is used as the primary example. Additional operations can be provided before, during, and after the method 100, and some operations described can be replaced, eliminated, or moved around for additional embodiments of the method.

FIGS. 2A through 2E are sectional views of a semiconductor structure 200 at various fabrication stages, constructed in accordance with some embodiments. The method 100 is described below in conjunction with FIG. 1 and FIGS. 2A through 2E wherein the semiconductor structure 200 is fabricated by using embodiments of the method 100. The semiconductor structure 200 may be an intermediate workpiece fabricated during processing of an IC, or a portion thereof, that may include logic circuits, memory structures, passive components (such as resistors, capacitors, and inductors), and active components such diodes, field-effect transistors (FETs), metal-oxide semiconductor field effect transistors (MOSFET), complementary metal-oxide semiconductor (CMOS) transistors, bipolar transistors, high voltage transistors, high frequency transistors, fin-like FETs (FinFETs), other three-dimensional (3D) FETs, metal-oxide semiconductor field effect transistors (MOSFET), complementary metal-oxide semiconductor (CMOS) transistors, bipolar transistors, high voltage transistors, high frequency transistors, other memory cells, and combinations thereof.

Referring now to FIG. 1 in conjunction with FIG. 2A, the method 100 begins at block 102 with a semiconductor structure 200. Referring to FIG. 2A, the semiconductor structure 200 includes a substrate 202. In an embodiment, the substrate 202 is a semiconductor substrate (e.g., wafer). In another embodiment, the substrate 202 includes silicon in a crystalline structure. In alternative embodiments, the substrate 202 includes other elementary semiconductors such as germanium, or a compound semiconductor such as silicon carbide, gallium arsenide, indium arsenide, and indium phosphide. The substrate 202 includes one or more layers of material or composition. The substrate 202 may include a silicon on insulator (SOI) substrate, be strained/stressed for performance enhancement, include epitaxial regions, include isolation regions, include doped regions, include one or more semiconductor devices or portions thereof, include conductive and/or non-conductive layers, and/or include other suitable features and layers.

In the present embodiment, the substrate 202 includes an underlayer (or material layer) 204 to be processed, such as to be patterned or to be implanted. For example, the underlayer 204 is a hard mask layer to be patterned. In another example, the underlayer 204 is an epitaxial semiconductor layer to be ion implanted. However, in an alternative embodiment, the substrate 202 may not include an underlayer. In an embodiment, the underlayer 204 is a hard mask layer including material(s) such as silicon oxide, silicon nitride (SiN), silicon oxynitride, or other suitable material or composition. In an embodiment, the underlayer 204 is an anti-reflection coating (ARC) layer such as a nitrogen-free anti-reflection coating (NFARC) layer including material(s) such as silicon oxide, silicon oxygen carbide, or plasma enhanced chemical vapor deposited silicon oxide. In various embodiments, the underlayer 204 may include a high-k dielectric layer, a gate layer, a hard mask layer, an interfacial layer, a capping layer, a diffusion/barrier layer, a dielectric layer, a conductive layer, other suitable layers, and/or combinations thereof.

In some embodiments, the structure 200 may be alternatively a photomask used to pattern a semiconductor wafer. In furtherance of the embodiments, the substrate 202 is a photomask substrate that may include a transparent material (such as quartz), or a low thermal expansion material such as silicon oxide-titanium oxide compound. The photomask substrate 202 may further include a material layer to be patterned. To further this example, the substrate 202 may be a photomask substrate for making a deep ultraviolet (DUV) mask, an extreme ultraviolet (EUV) mask, or other types of masks. Accordingly, the underlayer 204 is material layer to be patterned to define a circuit pattern. For example, the underlayer 204 is an absorber layer, such as chromium layer.

The method 100 proceeds to operation 104 with forming a photoresist layer (or simply resist layer) 206 over the substrate 202 (FIG. 2A). The resist layer 206 is sensitive to radiation used in a lithography exposure process and has a resistance to etch (or implantation). Referring to FIG. 2A, in an embodiment, the resist layer 206 is formed by spin-on coating process. In some embodiments, the resist layer 206 is further treated with a soft baking process. In some embodiments, the resist layer 206 is sensitive to a radiation, such as I-line light, a DUV light (e.g., 248 nm radiation by krypton fluoride (KrF) excimer laser or 193 nm radiation by argon fluoride (ArF) excimer laser), a EUV light (e.g., 135 nm light), an electron beam (e-beam), and an ion beam. In the present embodiment, the resist layer 206 is sensitive to EUV radiation.

Figure 3:
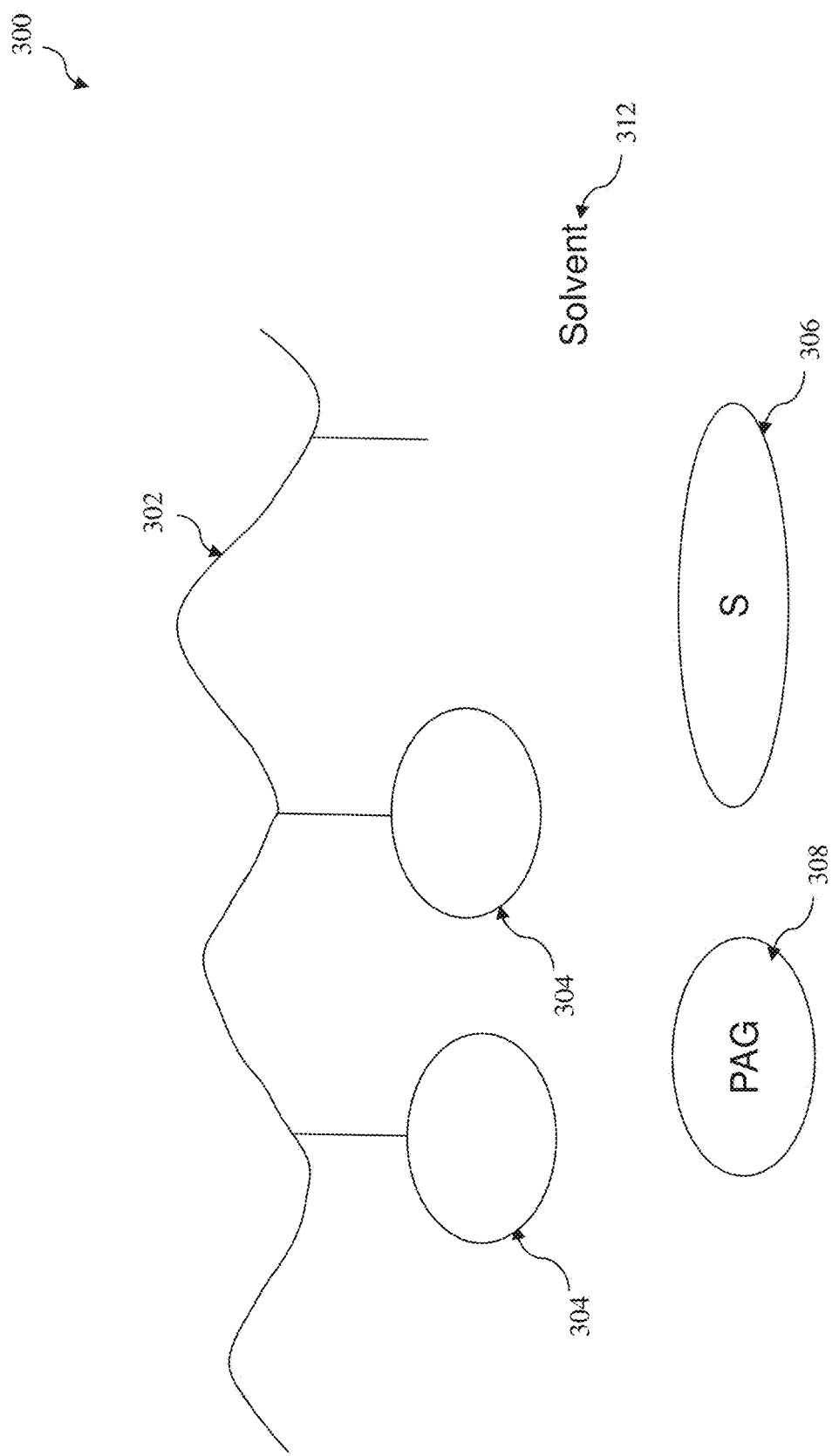
FIG. 3 illustrates a resist material of FIG. 2A in accordance with some embodiments.

FIG. 3 shows an embodiment of a resist material 300 of the resist layer 206, constructed in accordance with some embodiments. In the present example, the photoresist 300 utilizes a chemical amplification (CA) photoresist material. For example, the CA resist material is positive tone and includes a polymer material that turns soluble to a developer after the polymeric material is reacted with acid. In another example, the CA resist material is negative tone and includes a polymer material that turns insoluble to a developer such as a base solution after the polymer is reacted with acid. In yet another example, the CA resist material includes a polymer material that changes its polarity after the polymer is reacted with acid.

The resist material 300 is sensitive to a first radiation, such as extreme ultraviolet (EUV) light. The first radiation has a first wavelength. The resist material 300 includes a polymer 302, a blocking group 304 chemically bonded to the polymer 302, a sensitizer 306, and an acid generating compound 308. The resist material 300 further includes solvent 312 with above chemicals mixed therein. The sensitizer 306 could be blended or bonding in polymer 302. In some embodiments, the resist material 300 may include other additives, such as quencher.

Figures 4, 5:
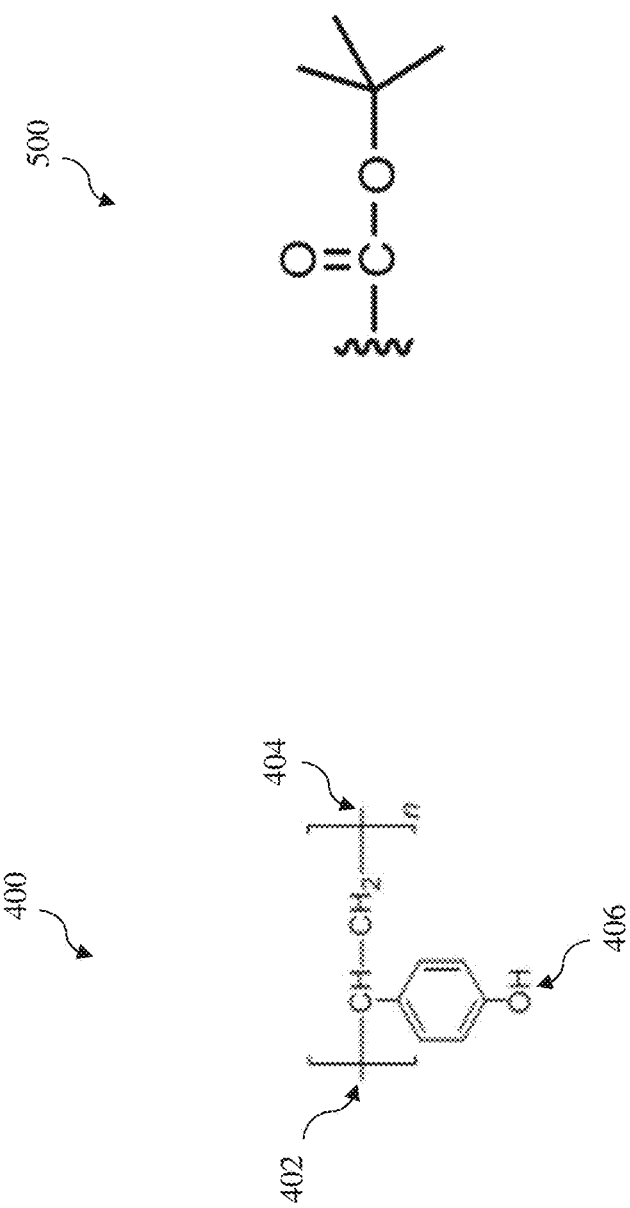
FIG. 4 illustrates a chemical structure of the polymer in the resist material of FIG. 3 in accordance with an embodiment.
FIG. 5 illustrates a chemical structure of the ALG in the resist material of FIG. 3 in accordance with an embodiment.

The polymer 302 provides resistance to etch (or implantation). In various embodiments, the polymer 302 includes a poly(norbornene)-co-malaic anhydride (COMA) polymer, a polyhydroxystyrene (PHS) polymer, or an acrylate-based polymer. For example, the acrylate-based polymer includes a poly (methyl methacrylate) (PMMA) polymer. The PHS polymer includes a plurality of PHS chemical structure 400 shown in FIG. 4, in which n is an integer greater than 2. The PHS chemical structure 400 includes two ends 402 and 404 that are chemically linkable ends of other PHS chemical structures. Furthermore, PHS is also sensitive to EUV and is able to function as sensitizer for EUV resist. Accordingly, a plurality of the chemical structures 400 are chemically bonded together (through the two ends 402 and 404), thereby forming a PHS polymeric backbone. The polymer 302 also includes multiple side locations that may chemically bond with other chemical groups. For example, the PHS polymer incudes a plurality of hydroxyl (OH) groups 406 chemically bonded to side locations.

In some examples, the resist material 300 further includes a blocking group 304, such as acid labile group (ALG) or dissolution inhibitor that responds to acid. The ALG 304 is a chemical group that is deprotected by PAG in exposed areas of the resist layer. Thus, the exposed resist material 300 will change the polarity and dissolubility. For example, the exposed resist material has an increased dissolubility in a developer (for a positive-tone resist) or decreased dissolubility in a developer (for a negative-tone resist). When the exposing dose of the lithography exposing process reaches a dose threshold, the exposed resist material will be dissoluble in the developer or alternatively the exposed resist material will be soluble in the developer. In one example, the ALG 304 includes a t-butoxycardbonyl (tBOC) 500 illustrated in FIG. 5.

The resist material 300 includes an acid generating compound 308, such as photoacid generator (PAG). The acid generating compound 308 absorbs radiation energy and generates acid. The resist material 300 also includes a solvent 312. The polymer 302 and the acid generating compound 308 are mixed in the solvent 312 before the resist material is applied to a workpiece, such as a semiconductor wafer, during a lithography process.

The resist material 300 further includes a sensitizer 306 to increase the sensitivity and efficiency of the resist material. The PAG in the resist material may not be sensitive to EUV but is more sensitive to electrons or other radiation, such UV or DUV. Thus, by incorporating the sensitizer 306, the resist material has an enhanced sensitivity to the first radiation. Particularly, the sensitizer 306 is sensitive to the first radiation and be able to generate a second radiation in response to the first radiation. In the present embodiment, the first radiation is EUV radiation and the second radiation is electron(s). The sensitizer 306 absorbs EUV radiation and generates secondary electron. Furthermore, the acid generating compound 308 is sensitive to the secondary electron, absorbs the secondary electron and generates acid. Additionally or alternatively, the sensitizer 306 absorbs the first radiation with a first wavelength and generates second radiation with a second wavelength. The second wavelength is greater than the first wavelength. In furtherance of the embodiment, the first radiation is EUV light and the first wavelength is about 13.5 nm; and the second wavelength ranges between 180 nm and 250 nm. In various examples, the sensitizer 306 includes a fluorine-containing chemical, a metal-containing chemical, a phenol-containing chemical or a combination thereof. In some examples, the sensitizer 306 includes a PHS chemical structure. In other examples, the sensitizer 306 includes polyhydroxystyrene, poly-fluorostyrene, or poly-chlorostyrene. The sensitizer 306 is mixed with the polymer 302 and the acid generator compound 308 in the solvent 312. The sensitizer 306 is alternatively or additionally bonded to the polymer 302. For example, some of the sensitizer is mixed with the polymer 302 and some of the sensitizer is chemically bonded to the polymer 302.

Back to the acid generating compound (or PAG) 308. The PAG 308 includes a phenyl ring. In a particular example, the PAG 308 includes a sulfonium cation, such as a triphenylsulfonium (TPS) group; and an anion, such as a triflate anion. Particularly, the cation of the PAG has a chemical bond to a sulfur and an additional chemical bond such that the sensitivity (or absorption) of the PAG to the electron, or other type of the second radiation, is increased.

Figure 6:
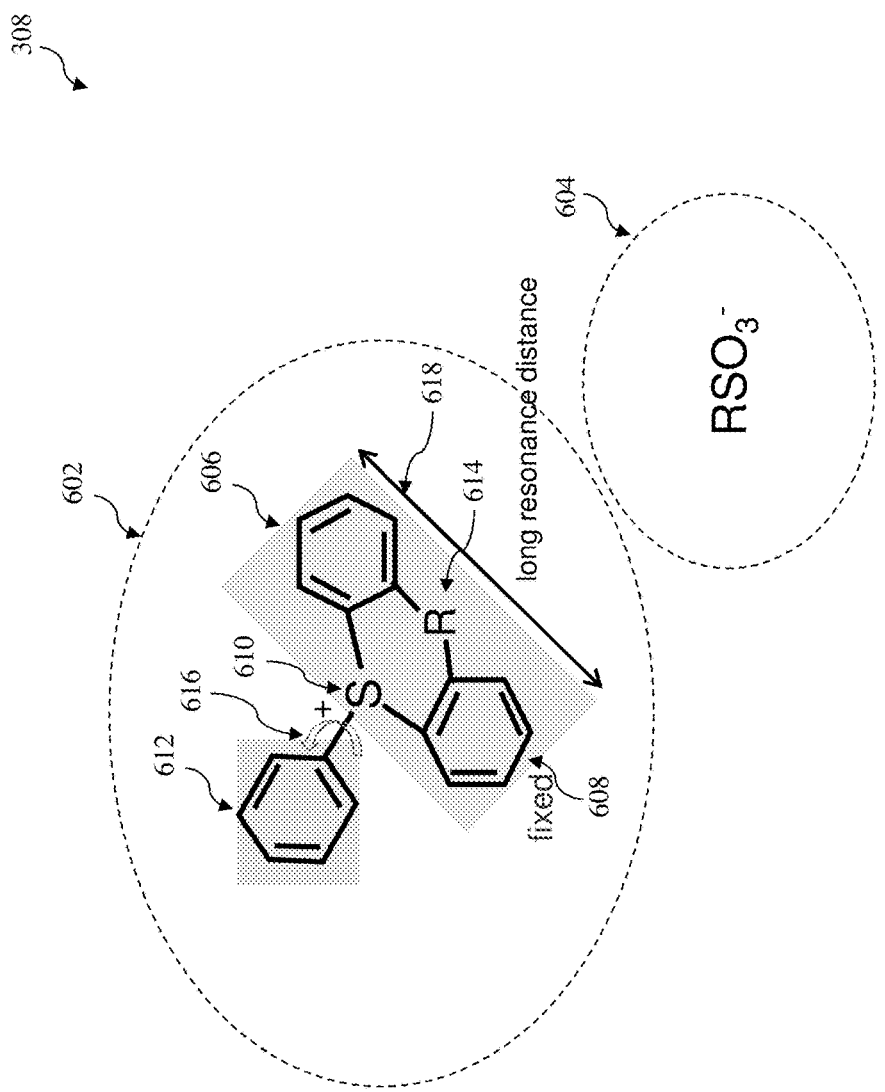
FIG. 6 illustrates a chemical structure of the PAG in the resist material of FIG. 3 in accordance with an embodiment.

The PAG structure is further described according to various examples. FIG. 6 illustrates the PAG 308, in part, constructed in accordance with some embodiments. The PAG 308 includes a cation 602 and anion 604. In some illustrated examples, the anion 604 includes one of a sulfonyl hydroxide and a fluoroalky sulfonyl hydroxide.

The cation 602 of the PAG 308 includes a first phenyl ring 606 and a second phenyl ring 608 chemically bonded to a sulfur 610. The cation 602 may include a third phenyl ring 612 chemically bonded to the sulfur 610. Especially, the first phenyl ring 606 and the second phenyl ring 608 are further chemically bonded, such as through a chemical group 614 or alternatively directly chemically bonded. Thus the dual chemical bonding of the first and second phenyl rings changes the structure of the cation, such as changing the motion freedom of the cation, thereby enhancing the absorption of the secondary electron. This can be understood by following explanation based on our experiments and analysis. Those phenyl rings bonding to the sulfur by a single bond connection provide various independent free rotations (such as 702, 704, and 706), which cause the three phenyl ring to exist in different plane and decreases the electron resonance distance 708, as illustrated in FIG. 7. In contrary, in the disclosed PAG 308 illustrated in FIG. 6, the cation 602 bridges the two phenyl rings (606 and 608) to reduce independent rotations (for example, independent rotations are reduced and limited to independent rotation 616). Therefore, it helps to prolong the resonance distance 618 and increase radical cation stability. Therefore, the secondary election is easier to be transferred to the cation and improve the quantum yield of acid generation. Accordingly, the sensitivity of the PAG 308 to the electron (or other type of the second radiation) is increased.

More particularly, the first phenyl ring 606 includes a first carbon and a second carbon adjacent to the first carbon and the second phenyl ring 608 includes a third carbon and a fourth carbon adjacent to the third carbon. The first carbon of the first phenyl ring 606 and the third carbon of the second phenyl ring 608 are chemically bonded to the sulfur, and the second carbon of the first phenyl ring 606 and the fourth carbon of the second phenyl ring 608 form an additional chemical bond through the chemical group 614. In various examples, the chemical structure R is a chemical group selected from the group consisting of a C1-C20 alkyl group, a cycloalkyl group, a hydroxyl alkyl group, an alkoxy group, an alkoxyl alkyl group, an acetyl group, an acetyl alkyl group, an carboxyl group, an alkyl caboxyl group, an cycloalkyl carboxyl group, a C2~C30 saturated hydrocarbon ring, a C2~C30 unsaturated hydrocarbon ring, a C2-C30 heterocyclic group, a 3-D chemical structure, or a combination thereof. In the above, the C1-C20 alkyl group stands for an alkyl group having a number ("n") of carbons, wherein the number n ranges from 1 to 20. Similarly, the C2~C30 saturated hydrocarbon ring stands for a saturated hydrocarbon ring having a number of carbons ranging from 2 to 30. In some examples, the C2-C30 heterocyclic group has one of a chain structure and a ring structure. In other examples, the 3-D chemical structure includes an adamantyl group. Alternatively, the second carbon and the fourth carbon are directly chemically bonded together.

Figure 8C:
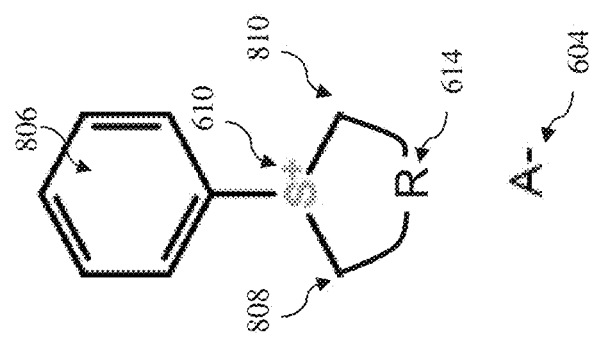
FIGS. 8A, 8B and 8C illustrate a chemical structure of the PAG of FIG. 6 in accordance with various embodiments.
Figure 8B:
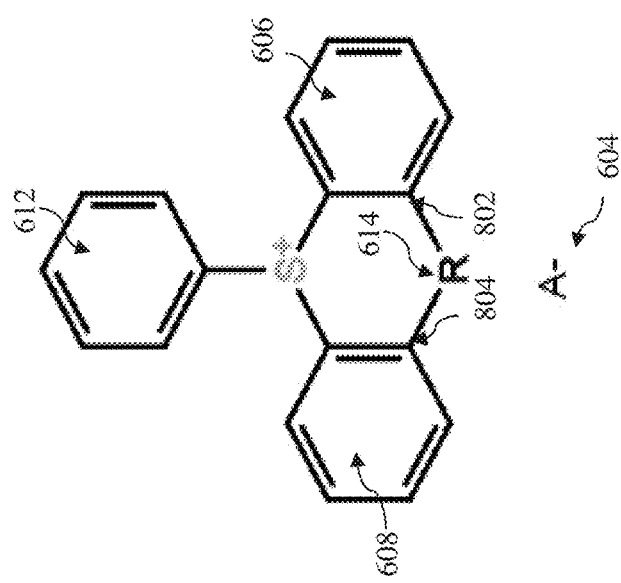
Figure 8A:
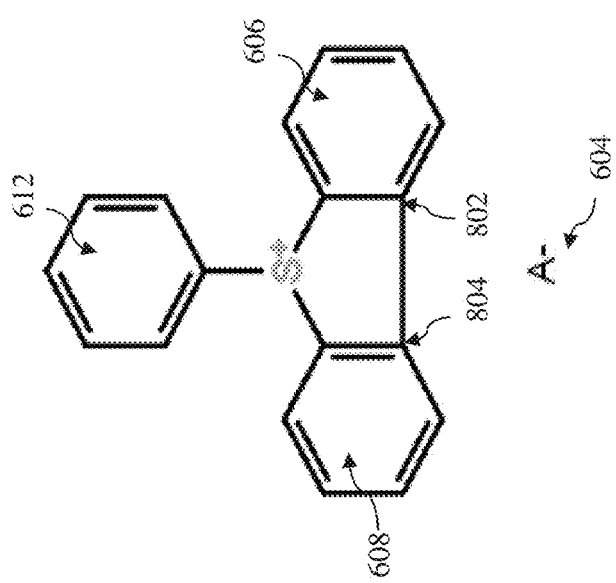

Additional bonding between the first phenyl ring and second phenyl ring increases the sensitivity of the PAG. Various examples are provided below. FIGS. 8A, 8B and 8C illustrate the structure of the PAG 308 constructed according to various examples. In one example illustrated in FIG. 8A, the PAG includes a cation 602 having three phenyl rings all chemically bonded to a sulfur element; and anion "A-" 604. Two of the phenyl rings are further chemically bonded. In the present case, the two of the phenyl rings are directly bonded, such as one carbon 802 of the first phenyl ring 606 and another carbon 804 of the second phenyl ring 608 are directly chemically bonded. In FIG. 8B, the PAG is similar to that of FIG. 8A except for that two phenyl rings are further chemically bonded through a chemical group R (labeled as 614), which is defined above. In FIG. 8C, the PAG includes a cation having a single phenyl ring 806 and a sulfur element 610 chemically bonded together. The sulfur element 610 is further bonded to two carbons 808 and 810. Those two carbons 808 and 810 are further chemically bonded through the chemical group R.

Figure 9A:
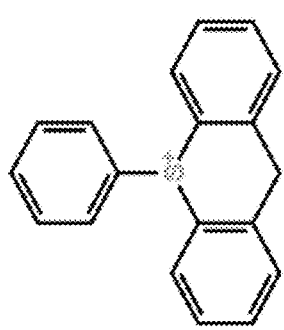
FIGS. 9A, 9B, 9C, 9D, 9E, 9F, 9G and 9H illustrate a chemical structure of the cation in the PAG of FIG. 6 in accordance with some embodiments.
Figure 9B:
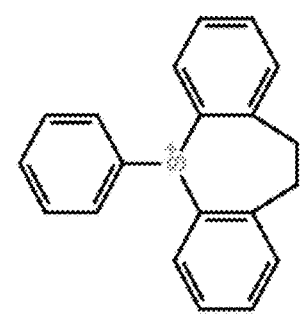
Figure 9C:
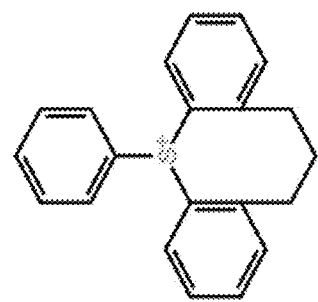
Figure 9D:
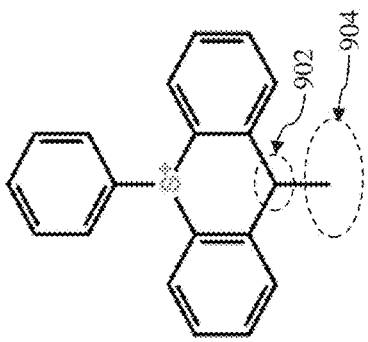
Figure 9E:
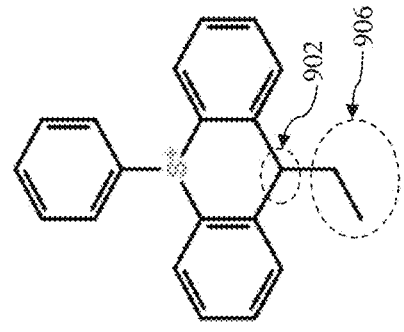
Figure 9F:
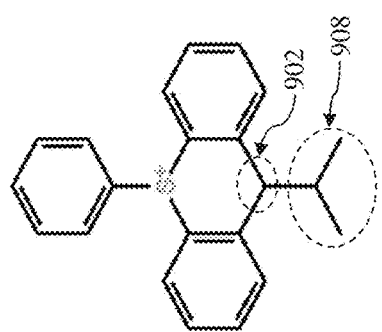
Figure 9G:
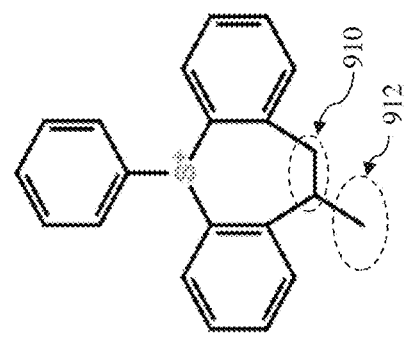
Figure 9H:
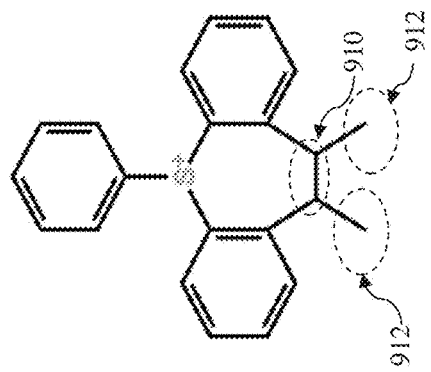

FIGS. 9A though 9H illustrate the cation 602 of the PAG 308, constructed according to various embodiments. The cation 602 includes a first phenyl ring, a second phenyl ring and a third phenyl ring all chemically bonded to a sulfur element. The first and second phenyl rings form a second chemical bond through different chemical structures, such as one carbon as illustrated in FIG. 9A; two carbons as illustrated in FIG. 9B; or three carbons as illustrated in FIG. 9C. In addition to the second chemical bonding, the cation 602 may further include other chemical structures, such as those illustrated in FIGS. 9D to 9H. For example in FIG. 9D, two phenyl rings are bonded to the sulfur and are further bonded together through a carbon 902, which is further bonded to another carbon 904 or a chemical structure. In FIG. 9E, two phenyl rings are bonded to the sulfur and further bonded through a carbon 902, which is further bonded to a chemical structure 906 having two carbons. In FIG. 9F, two phenyl rings are bonded to the sulfur and further bonded through a carbon 902, which is further bonded to a chemical structure 908 having three carbons. In FIG. 9G, two phenyl rings are bonded to the sulfur and further bonded through two carbons 902, one of the two carbons 902 being further bonded to a carbon 912 or a chemical structure. In FIG. 9H, two phenyl rings are bonded to the sulfur and further bonded through two carbons 902, each being further bonded to a carbon 912 or a chemical structure.

Figure 10C:
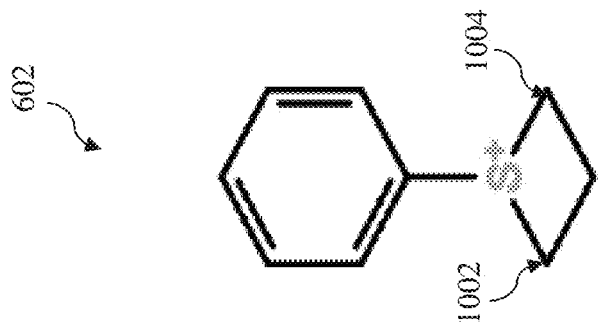
FIGS. 10A, 10B and 10C illustrate a chemical structure of the cation in the PAG of FIG. 6 in accordance with some embodiments.
Figure 10B:
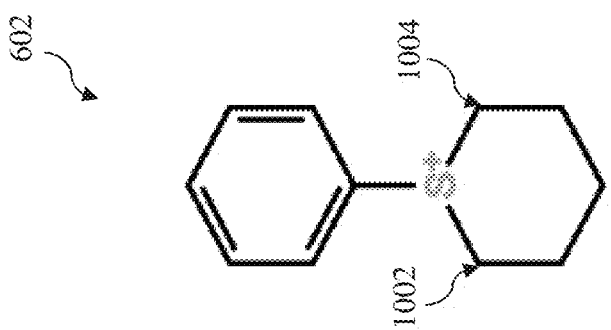
Figure 10A:
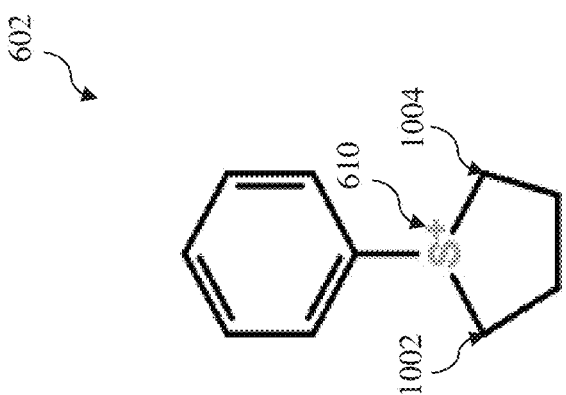

FIGS. 10A though 10C illustrate the cation 602 of the PAG 308, constructed according to various other examples. Those can be considered as different examples of the cation 602 in FIG. 8C. The cation 602 includes a phenyl ring and sulfur 610 chemically bonded together. The sulfur 610 is further chemically bonded to series of carbons (4 carbons in FIG. 10A; 5 carbons in FIG. 10B; and 3 carbons in FIG. 10C), in a closed ring. Particularly, the sulfur 610 is further bonded to two carbons 1002 and 1004. Those two carbons 1002 and 1004 are further chemically bonded through the chemical group R, such as two carbons in FIG. 10A, three carbons in FIG. 10B and one carbon in FIG. 10C, respectively. It is noted that each cation structure includes a phenyl ring and a second ring. However, the second ring is a heterocyclic compound that includes sulfur and carbons. For example, the cation 602 in FIG. 10A includes a thiophene bonded to the phenyl ring though the sulfur.

Referring to FIGS. 1 and 2B, the method 100 proceeds to operation 106 by performing an exposing process to the resist layer 206 to the first radiation beam in a lithography system. In some embodiments, the first radiation is a EUV radiation (e.g., 13.5 nm). In some embodiments, the first radiation may be an I-line (365 nm), a DUV radiation such as KrF excimer laser (248 nm), ArF excimer laser (193 nm), a EUV radiation, an x-ray, an e-beam, an ion beam, and/or other suitable radiations. The operation 106 may be performed in air, in a liquid (immersion lithography), or in a vacuum (e.g., for EUV lithography and e-beam lithography). In some embodiments, the radiation beam is directed to the resist layer 206 to form an image of a circuit pattern defined on a photomask, such as a transmissive mask or a reflective mask in a proper exposing mode, such as step and scan. Various resolution enhancement techniques, such as phase-shifting, off-axis illumination (OAI) and/or optical proximity correction (OPC), may be used implemented through the photomask or the exposing process. For examples, the OPC features may be incorporated into the circuit pattern. In another example, the photomask is a phase-shift mask, such as an alternative phase-shift mask, an attenuated phase-shift mask, or a chromeless phase-shift mask. In yet another example, the exposing process is implemented in an off-axis illumination mode. In some other embodiments, the radiation beam is directly modulated with a predefined pattern, such as an IC layout, without using a mask (such as using a digital pattern generator or direct-write mode). In the present embodiment, the radiation beam is a EUV radiation and the operation 106 is performed in a EUV lithography system, such as the EUV lithography system. Since the sensitivity of the resist layer 206 is enhanced and the exposing threshold of the resist layer may be lower than 20 mJ/cm$^2$. Accordingly, the exposing process is implemented with the dose less than 20 mJ/cm$^2$.

Still referring to the operation 106, after the exposure, the operation 106 may further include other steps, such as thermal treatment. In the present embodiment, the operation 106 includes a post-exposure baking (PEB) process to the semiconductor structure 200, especially to the resist layer 206 coated on the substrate 202. During the PEB process, the ALG 304 in the exposed resist material is cleaved, the exposed portions of the resist material 300 are changed chemically (such as more hydrophilic or more hydrophobic). In a specific embodiment, the PEB process may be performed in a thermal chamber at temperature ranging between about 120° C. to about 160° C.

After the operation 106, a latent pattern is formed on the resist layer 206. The latent pattern of a resist layer refers to the exposed pattern on the resist layer, which eventually becomes a physical resist pattern, such as by a developing process. The latent pattern of the resist layer 206 includes unexposed portions 206a and exposed portions 206. In the present case, of the latent pattern, the exposed portions 206b of the resist layer 206 are physically or chemically changed. In some examples, the exposed portions 206b are de-protected, inducing polarity change for dual-tone imaging (developing). In other examples, the exposed portions 206b are changed in polymerization, such as depolymerized as in positive resist or cross-linked as in negative resist.

Referring to FIGS. 1 and 2C, the method 100 then proceeds to operation 108 by developing the exposed resist layer 206 in a developer, constructed in accordance with some embodiments. By the developing process, a patterned resist layer 206' is formed. In some embodiments, the resist layer 206 experiences a polarity change after the operation 106, and a dual-tone developing process may be implemented. In some examples, the resist layer 206 is changed from a nonpolar state (hydrophobic state) to a polar state (hydrophilic state), then the exposed portions 206b will be removed by an aqueous solvent (positive tone imaging), such as tetramethyl ammonium hydroxide (TMAH), or alternatively the unexposed portions 206a will be removed by an organic solvent (negative tone imaging), such as butyl acetate. In some other examples, the resist layer 206 is changed from a polar state to a nonpolar state, then the exposed portions 206b will be removed by an organic solvent (positive tone imaging) or the unexposed portions 206a will be removed by an aqueous solvent (negative tone imaging).

In the present example illustrated in FIG. 2C, the unexposed portions 206a are removed in the developing process. In this example shown in FIG. 2C, the patterned resist layer 206' is represented by two line patterns. However, the following discussion is equally applicable to resist patterns represented by trenches.

Referring to FIGS. 1 and 2D, the method 100 includes an operation 110 by performing a fabrication process to the semiconductor structure 200 using the patterned resist layer 206' as a mask such that the fabrication process is only applied to the portions of the semiconductor structure 200 within the openings of the patterned resist layer 206' while other portions covered by the patterned resist layer 206' are protected from being impacted by the fabrication process. In some embodiments, the fabrication process includes an etching process applied to the material layer 204 using the patterned resist layer 206' as an etch mask, thereby transferring the pattern from the patterned resist layer 206' to the material layer 204. In alternative embodiments, the fabrication process includes an ion implantation process applied to the semiconductor structure 200 using the patterned resist layer as an implantation mask, thereby forming various doped features in the semiconductor structure 200.

Figure 2E:
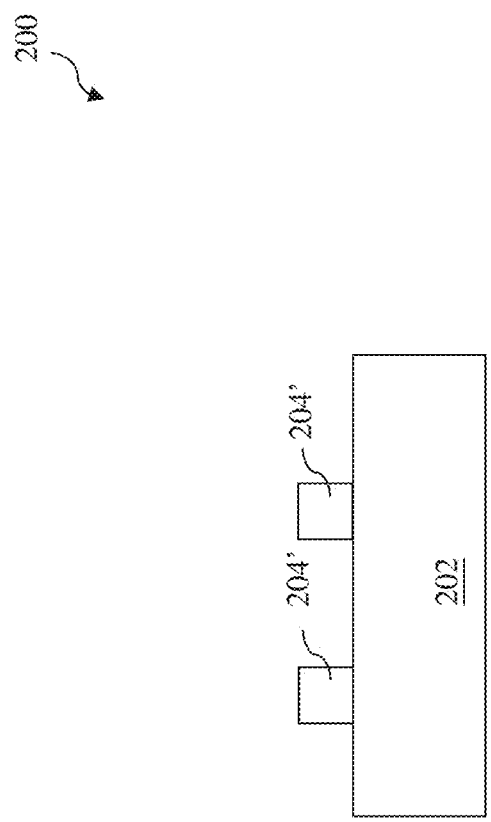

In the present example, the material layer 204 is a hard mask layer. To further this embodiment, the pattern is first transferred from the patterned resist layer 206' to the hard mask layer 204, then to other layers of the substrate 202. For example, the hard mask layer 204 may be etched through openings of the patterned resist layer 206' using a dry (plasma) etching, a wet etching, and/or other etching methods. For example, a dry etching process may implement an oxygen-containing gas, a fluorine-containing gas, a chlorine-containing gas, a bromine-containing gas, an iodine-containing gas, other suitable gases and/or plasmas, and/or combinations thereof. The patterned resist layer 206' may be partially or completely consumed during the etching of the hard mask layer 204. In an embodiment, any remaining portion of the patterned resist layer 206' may be stripped off, leaving a patterned hard mask layer 204' over the substrate 202, as illustrated in FIG. 2E.

Although not shown in FIG. 1, the method 100 may include other operations before, during or after the operations described above. In an embodiment, the substrate 202 is a semiconductor substrate and the method 100 proceeds to forming fin field effect transistor (FinFET) structures. In this embodiment, the method 100 includes forming a plurality of active fins in the semiconductor substrate 202. In furtherance of the embodiment, the operation 110 further includes etching the substrate 202 through the openings of the patterned hard mask 204' to form trenches in the substrate 202; filling the trenches with a dielectric material; performing a chemical mechanical polishing (CMP) process to form shallow trench isolation (STI) features; and epitaxy growing or recessing the STI features to form fin-like active regions. In another embodiment, the method 100 includes other operations to form a plurality of gate electrodes in the semiconductor substrate 202. The method 100 may further form gate spacers, doped source/drain regions, contacts for gate/source/drain features, etc. In another embodiment, a target pattern is to be formed as metal lines in a multilayer interconnection structure. For example, the metal lines may be formed in an inter-layer dielectric (ILD) layer of the substrate 202, which has been etched by operation 110 to form a plurality of trenches. The method 100 proceeds to filling the trenches with a conductive material, such as a metal; and further proceeds to polishing the conductive material using a process such as chemical mechanical planarization (CMP) to expose the patterned ILD layer, thereby forming the metal lines in the ILD layer. The above are non-limiting examples of devices/structures that can be made and/or improved using the method 100 and the material layer 206 according to various aspects of the present disclosure.

The present disclosure provides a photoresist material with enhanced sensitivity and a lithography method using the same. The resist material includes a polymer, a sensitizer and a PAG mixed in a solvent. More specifically, the PAG includes a phenyl ring bonded to sulfur with an additional chemical bond for increased resonance distance and increased absorption to secondary electrons or other type of the second radiation. Accordingly, the sensitivity of the resist material is enhanced.

Thus, the present disclosure provides a method for lithography patterning in accordance with some embodiments. The method includes forming a photoresist layer over a substrate, wherein the photoresist layer includes a polymer, a sensitizer, and a photo-acid generator (PAG), wherein the PAG includes a first phenyl ring and a second phenyl ring both chemically bonded to a sulfur, the first and second phenyl rings being further chemically bonded with enhanced sensitivity; performing an exposing process to the photoresist layer; and developing the photoresist layer, thereby forming a patterned photoresist layer.

The present disclosure provides a method for lithography patterning in accordance with some embodiments. The method includes forming a photoresist layer over a substrate, wherein the photoresist layer includes a polymer, a sensitizer, and a photo-acid generator (PAG), wherein the PAG includes a first phenyl ring and a sulfur chemically bonded together, wherein the sulfur is further chemically bonded to a first carbon and a second carbon that are chemically bonded together; performing an exposing process to the photoresist layer; and developing the photoresist layer, thereby forming a patterned photoresist layer.

The present disclosure provides a method for lithography patterning in accordance with some embodiments. The method includes forming a photoresist layer over a substrate, wherein the photoresist layer includes a polymer; a sensitizer that is sensitive to an extreme ultraviolet (EUV) radiation and is able to generate an electron in response to the EUV radiation; and a photo-acid generator (PAG) that is able to generate an acid in response to the electron, wherein the PAG includes a first phenyl ring and a second phenyl ring bother chemically bonded to a sulfur, the first and second phenyl rings being further chemically bonded with enhanced sensitivity; performing an exposing process to the photoresist layer to the EUV radiation; and developing the photoresist layer, thereby forming a patterned photoresist layer.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A method for lithography patterning, comprising:
    forming a photoresist layer over a substrate, wherein the photoresist layer includes a polymer, a sensitizer that includes a polyhydroxystyrene (PHS) chemical group, and a photo-acid generator (PAG), wherein the PAG includes a first phenyl ring and a second phenyl ring both chemically bonded to a sulfur, the first and second phenyl rings being further chemically bonded with enhanced sensitivity;
    performing an exposing process to the photoresist layer; and
    developing the photoresist layer, thereby forming a patterned photoresist layer.

2. The method of claim 1, wherein the first phenyl ring includes a first carbon and a second carbon adjacent to the first carbon and the second phenyl ring includes a third carbon and a fourth carbon adjacent to the third carbon, wherein the first carbon of the first phenyl ring and the third carbon of the second phenyl ring are chemically bonded to the sulfur, and the second carbon of the first phenyl ring and the fourth carbon of the second phenyl ring are chemically bonded.

3. The method of claim 2, wherein the second carbon of the first phenyl ring and the fourth carbon of the second phenyl ring are directly chemically bonded together.

4. The method of claim 3, wherein the second carbon of the first phenyl ring and the fourth carbon of the second phenyl ring are chemically bonded to a chemical structure R, wherein the chemical structure R is a chemical group selected from the group consisting of a C1-C20 alkyl group, a cycloalkyl group, a hydroxyl alkyl group, an alkoxy group, an alkoxyl alkyl group, an acetyl group, an acetyl alkyl group, an carboxyl group, an alkyl caboxyl group, an cycloalkyl carboxyl group, a C2~C30 saturated hydrocarbon ring, a C2~C30 unsaturated hydrocarbon ring, a C2-C30 heterocyclic group, a 3-D chemical structure.

5. The method of claim 4, wherein the C2-C30 heterocyclic group has one of a chain structure and a ring structure, wherein the 3-D chemical structure includes an adamantyl group.

6. The method of claim 2, wherein the PAG further includes a third phenyl ring chemically bonded to the sulfur.

7. The method of claim 2, wherein the PAG further includes an anion A-, which is one of a sulfonyl hydroxide and a fluoroalky sulfonyl hydroxide.

8. The method of claim 1, wherein the PAG includes a chemical structure selected from the group consisting of following structures

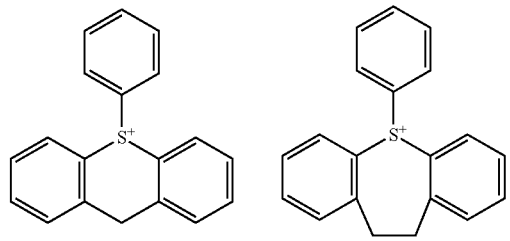

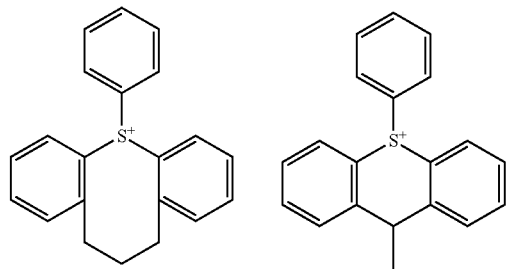

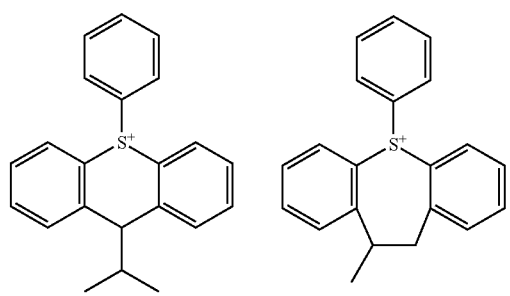

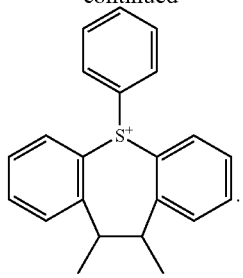

9. The method of claim 1, wherein
the performing of the exposing process to the photoresist layer includes exposing a portion of the photoresist layer to an extreme ultraviolet (EUV) radiation;
the sensitizer is sensitive to the EUV radiation and is able to generate an electron in response to the EUV radiation; and
the PAG is able to generate an acid in response to the electron.

10. The method of claim 1, wherein
the sensitizer includes a phenol group; and
the polymer includes one of an acrylate-based polymer, a poly(norbornene)-co-malaic anhydride (COMA) polymer, and a polyhydroxystyrene (PHS) polymer.

11. The method of claim 1, wherein the sensitizer includes one of a fluorine-containing chemical, a metal-containing chemical, a phenol-containing chemical, and a combination thereof.

12. The method of claim 1, wherein the polymer includes a polyhydroxystyrene (PHS) polymer and the sensitizer is bonded to the polymer.

13. A method for lithography patterning, comprising:
forming a photoresist layer over a substrate, wherein the photoresist layer includes a polymer that includes a polyhydroxystyrene (PHS) polymer, a sensitizer that is bonded to the polymer, and a photo-acid generator (PAG), wherein the PAG includes a first phenyl ring and a sulfur chemically bonded together, wherein the sulfur is further chemically bonded to a first carbon and a second carbon that are chemically bonded together;
performing an exposing process to the photoresist layer; and
developing the photoresist layer, thereby forming a patterned photoresist layer.

14. The method of claim 13, wherein the first carbon and the second carbon are chemically bonded together through another carbon.

15. The method of claim 13, wherein the first carbon and the second carbon are chemically bonded together through a plurality of carbons, wherein the plurality of carbons, the first carbon and the second carbon are configured in a cycloalkane structure.

16. The method of claim 13, wherein the first carbon is configured in a second phenyl ring and the second carbon is configured in a third phenyl ring.

17. The method of claim 16, wherein the second phenyl ring further includes a third carbon adjacent to the first carbon and the third phenyl ring further includes a fourth carbon adjacent to the second carbon, wherein the third carbon of the second phenyl ring and the fourth carbon of the third phenyl ring are chemically bonded to a chemical structure R, wherein the chemical structure R is a chemical group selected from the group consisting of a C1-C20 alkyl group having a number of carbons, a cycloalkyl group, a hydroxyl alkyl group, an alkoxy group, an alkoxyl alkyl group, an acetyl group, an acetyl alkyl group, an carboxyl group, an alkyl caboxyl group, an cycloalkyl carboxyl group, a C2~C30 saturated hydrocarbon ring, a C2~C30 unsaturated hydrocarbon ring, a C2-C30 heterocyclic group, a 3-D chemical structure.

18. A method for lithography patterning, comprising:
forming a photoresist layer over a substrate, wherein the photoresist layer includes a polyhydroxystyrene (PHS) polymer; a sensitizer that includes a PHS chemical structure and is sensitive to an extreme ultraviolet (EUV) radiation and is able to generate an electron in response to the EUV radiation; and a photo-acid generator (PAG) that is able to generate an acid in response to the electron, wherein the PAG includes a first phenyl ring and a second phenyl ring both chemically bonded to a sulfur, the first and second phenyl rings being further chemically bonded with enhanced sensitivity;
performing an exposing process to the photoresist layer to the EUV radiation; and
developing the photoresist layer, thereby forming a patterned photoresist layer.

19. The method of claim 18, wherein
the sensitizer includes one of a fluorine-containing chemical, a metal-containing chemical, a phenol-containing chemical, and a combination thereof; and
the polymer includes one of an acrylate-based polymer, and a poly(norbornene)-co-malaic anhydride (COMA) polymer.

20. The method of claim 18, wherein the first phenyl ring includes a first carbon and a second carbon adjacent to the first carbon and the second phenyl ring includes a third carbon and a fourth carbon adjacent to the third carbon, wherein the first carbon of the first phenyl ring and the third carbon of the second phenyl ring are chemically bonded to the sulfur, and the second carbon of the first phenyl ring and the fourth carbon of the second phenyl ring are chemically bonded to a chemical structure R, wherein the chemical structure R is a chemical group selected from the group consisting of a C1-C20 alkyl group having a number of carbons, a cycloalkyl group, a hydroxyl alkyl group, an alkoxy group, an alkoxyl alkyl group, an acetyl group, an acetyl alkyl group, an carboxyl group, an alkyl caboxyl group, an cycloalkyl carboxyl group, a C2~C30 saturated hydrocarbon ring, a C2~C30 unsaturated hydrocarbon ring, a C2-C30 heterocyclic group, a 3-D chemical structure.

* * * * *